(12) United States Patent
Mast

(10) Patent No.: US 10,676,907 B2
(45) Date of Patent: Jun. 9, 2020

(54) ORGANIC WASTE TREATMENT PROCESS AND DEVICE

(71) Applicant: David Jay Mast, Germantown, MD (US)

(72) Inventor: David Jay Mast, Germantown, MD (US)

( * ) Notice: Subject to any disclaimer, the term of this patent is extended or adjusted under 35 U.S.C. 154(b) by 176 days.

(21) Appl. No.: 16/076,785

(22) PCT Filed: Jun. 19, 2017

(86) PCT No.: PCT/US2017/038191
§ 371 (c)(1),
(2) Date: Aug. 9, 2018

(87) PCT Pub. No.: WO2018/236340
PCT Pub. Date: Dec. 27, 2018

(65) Prior Publication Data
US 2019/0161953 A1    May 30, 2019

(51) Int. Cl.
*E03D 9/10*   (2006.01)
*C02F 9/00*   (2006.01)
(Continued)

(52) U.S. Cl.
CPC .................. *E03D 9/10* (2013.01); *A47K 11/00* (2013.01); *A47K 11/02* (2013.01); *C02F 9/00* (2013.01);
(Continued)

(58) Field of Classification Search
USPC .......... 435/290.3; 4/479, 484, 499; 210/259, 210/603
See application file for complete search history.

(56) References Cited

U.S. PATENT DOCUMENTS 420,332 A     5/1889  Carrico
3,462,275 A *  8/1969  Bellamy ................. A23K 10/12
                                                   426/53
(Continued)

FOREIGN PATENT DOCUMENTS

WO    WO1994029014    * 12/1994

OTHER PUBLICATIONS

U.S.EPA. A Plain English Guide to the EPA Part 503 Biosolids Rule, EPA/832-R-93-003, Sep. 1994, p. 4.
(Continued)

*Primary Examiner* — Nina Bhat

(57) ABSTRACT

A thermophilic enzymatic biosynthesis (TEBS) device (50) produces outputs of newly synthesized substances, stabilized matter and fully recovered organic material, wherein the preferred device is a dry closet employing multistage treatment of organic solid, liquid and gaseous wastes. Said contemplated device comprises a multiphase thermophilic environment chamber (MTEC) (1) having a mixing zone (4), a cultivation zone (12), a pasteurization zone (24) and a germination zone (7) which utilizes a multiphase germination (62). The device comprises a thermodynamic pathway (29) and a functional respiration (64) which is directed toward an ammine reaction chamber (ARC) (3), which includes an oxidation surface (47) having reactivity with ammonia, producing a metal ammine complex. The device further comprises a subterranean uptake chamber (SUC) (2) which includes a plant growth medium (44) where gases received from the ARC (3) disperse to an uptake root structure (46), thereby reducing carbon dioxide emissions.

13 Claims, 9 Drawing Sheets

(51) Int. Cl.
    *C05F 3/06*         (2006.01)
    *C05F 3/04*         (2006.01)
    *C05F 3/00*         (2006.01)
    *A47K 11/00*       (2006.01)
    *C12M 1/02*         (2006.01)
    *C05C 3/00*         (2006.01)
    *C05F 17/10*       (2020.01)
    *C05F 17/90*       (2020.01)
    *A47K 11/02*       (2006.01)
    *C12M 1/00*         (2006.01)
    *C12M 1/06*         (2006.01)
    *C12M 1/33*         (2006.01)
    *C02F 1/28*         (2006.01)
    *C02F 1/02*         (2006.01)
    *C02F 103/00*       (2006.01)
    *C02F 101/16*       (2006.01)
    *C02F 3/12*         (2006.01)
    *C02F 3/32*         (2006.01)
    *C02F 1/20*         (2006.01)
    *C02F 3/34*         (2006.01)

(52) U.S. Cl.
CPC ............... *C05C 3/005* (2013.01); *C05F 3/00* (2013.01); *C05F 3/04* (2013.01); *C05F 3/06* (2013.01); *C05F 17/15* (2020.01); *C05F 17/90* (2020.01); *C12M 1/02* (2013.01); *C12M 23/30* (2013.01); *C12M 27/02* (2013.01); *C12M 45/02* (2013.01); *C02F 1/02* (2013.01); *C02F 1/20* (2013.01); *C02F 1/283* (2013.01); *C02F 3/12* (2013.01); *C02F 3/1284* (2013.01); *C02F 3/327* (2013.01); *C02F 3/348* (2013.01); *C02F 2101/16* (2013.01); *C02F 2103/005* (2013.01); *C02F 2301/106* (2013.01); *C02F 2303/02* (2013.01); *C02F 2303/04* (2013.01); *C02F 2303/26* (2013.01); *C02F 2305/06* (2013.01)

(56) References Cited

U.S. PATENT DOCUMENTS

| | | | | |
|---|---|---|---|---|
| 3,959,829 A * | 6/1976 | Nordgren | ............... | A47K 11/02 4/111.2 |
| 4,343,051 A | 8/1982 | Persson | | |
| 4,364,130 A * | 12/1982 | Persson | ............... | C05F 3/04 4/449 |
| 4,521,304 A * | 6/1985 | Yount | ............... | A47K 11/02 210/96.1 |
| 5,303,431 A * | 4/1994 | Johansson | ............... | C05F 3/04 4/449 |
| 5,418,982 A * | 5/1995 | Kishi | ............... | E03D 11/11 4/111.1 |
| 5,501,978 A * | 3/1996 | Sundberg | ............... | A47K 11/02 435/290.3 |
| 6,047,414 A * | 4/2000 | Bailey | ............... | A47K 11/02 4/484 |
| 6,184,014 B1 | 2/2001 | Echigo | | |
| 6,420,167 B1 * | 7/2002 | Okamoto | ............... | C05F 9/02 435/286.6 |
| 8,092,680 B2 * | 1/2012 | Johnson | ............... | C12P 5/023 210/603 |
| 9,247,852 B2 * | 2/2016 | Trott | ............... | A47K 11/02 |
| 9,663,392 B2 * | 5/2017 | Nicoletti | ............... | C05F 17/20 |
| 10,155,699 B2 * | 12/2018 | Sim | ............... | C05B 17/00 |
| 10,294,448 B1 * | 5/2019 | Bruce | ............... | C12M 47/10 |
| 10,358,809 B2 * | 7/2019 | Snyder | ............... | B60R 15/04 |
| 2003/0153071 A1 * | 8/2003 | Sattler | ............... | C05F 17/964 435/289.1 |
| 2009/0038066 A1 * | 2/2009 | Kallmann | ............... | A47K 11/02 4/479 |
| 2010/0275362 A1 * | 11/2010 | Biesinger | ............... | A47K 11/02 4/483 |
| 2013/0130346 A1 * | 5/2013 | Hansen | ............... | B09B 3/00 435/167 |

OTHER PUBLICATIONS

U.S.EPA. Environmental Regulations and Technology Control of Pathogens and Vector Attraction in Sewage Sludge, EPA/625/R-92/013, Revised Jul. 2003, p. 13,26,32,54,58,61,7.

U.S.EPA. Water Efficiency Technology Fact Sheet Composting Toilets, EPA 832-F-99-066, Sep. 1999, p. 6.

Kristen M. DeAngelis et al. Characterization of Trapped Lignin-Degrading Microbes in Tropical Forest Soil, http://doi.org/ 10.1371/journal.pone.0019306, 2011, p. 1.

Holwerda EK, Ellis LD, Lynd LR., et al. Development and Evaluation of methods to Infer Biosynthesis and Substrate Consumption in Cultures of Cellulolytic Microorganisms, Biotechnology and Bioengineering. 2013, p. 4.

\* cited by examiner

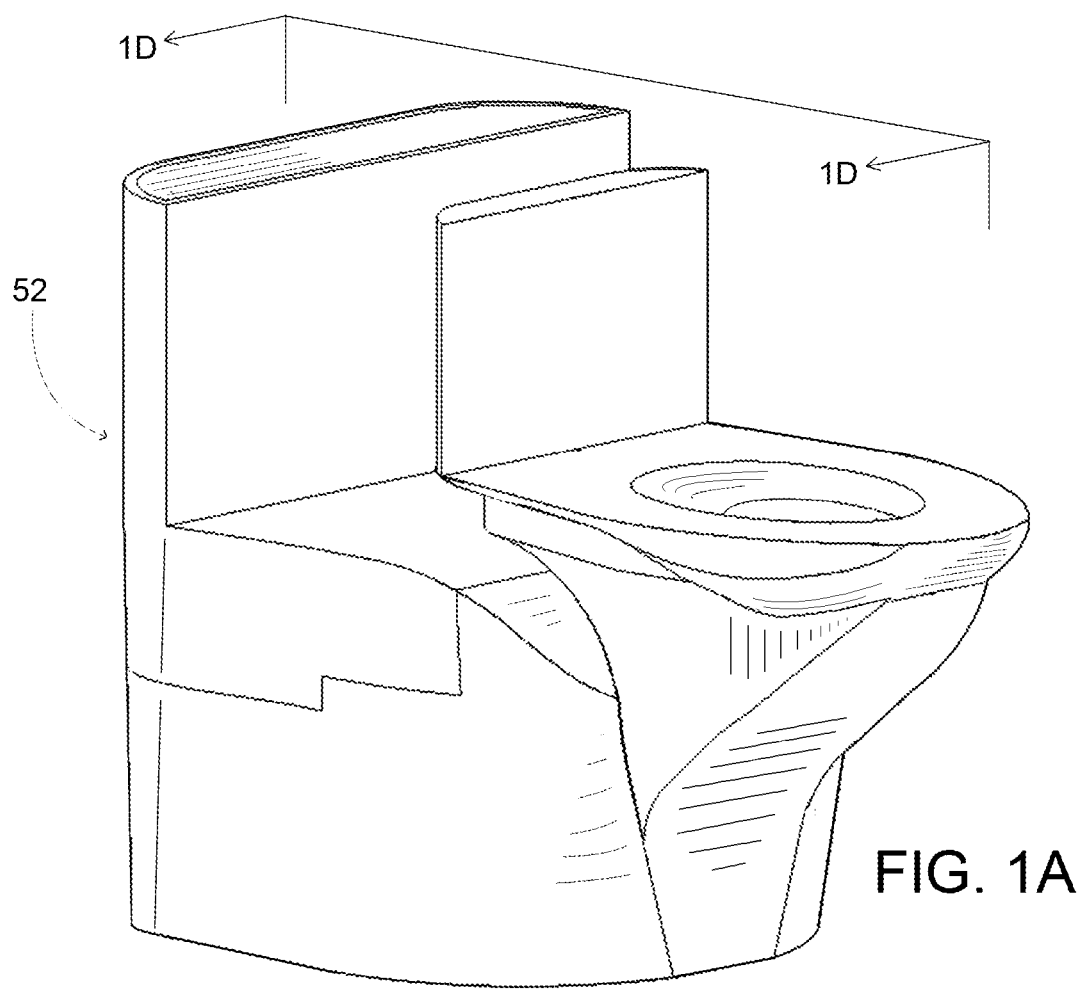
FIG. 1A
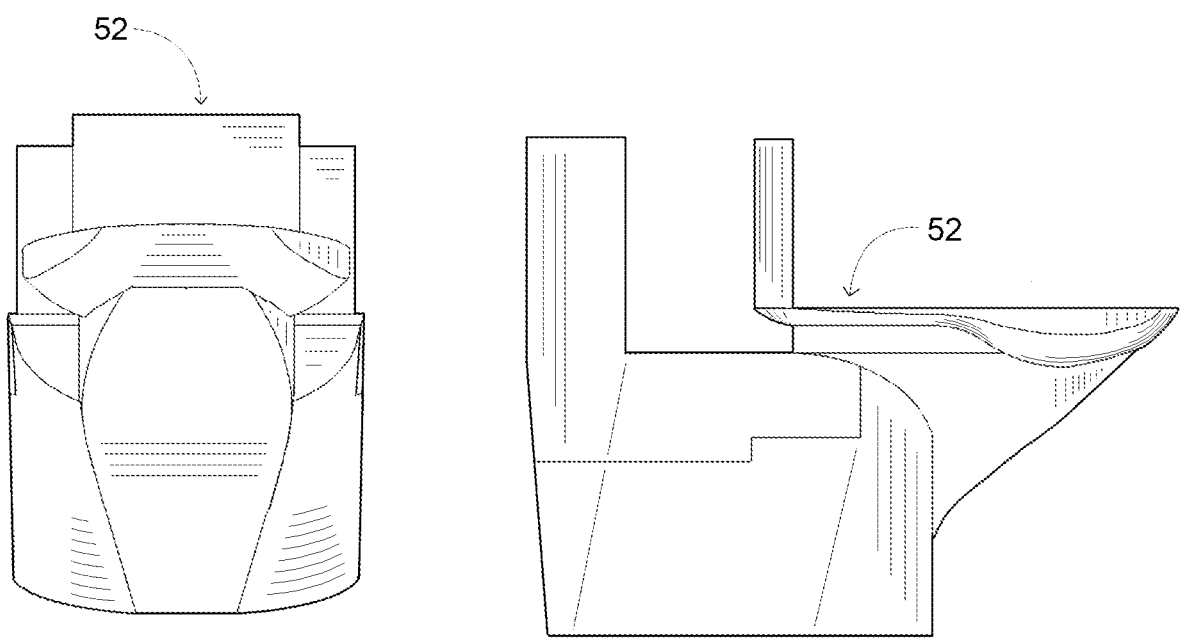
FIG. 1B
FIG. 1C

ORGANIC WASTE TREATMENT PROCESS AND DEVICE

TECHNICAL FIELD

This invention relates to a treatment process for organic waste recovery, having particular application to a new type of dry closet device which makes use of highly efficient accelerated germination and recovery of organic waste gases for an improved point of use system. This present invention has application for meeting the standards set by the U.S. Environmental Protection Agency (EPA) for exceptional quality (EQ) Class A Biosolids.

BACKGROUND ART

Global efforts exist to develop environmentally sustainable technologies for organic waste recovery.

In modern society, waste treatment systems have played an important role in reducing diseases caused by contamination of the water supply by pathogens. The introduction of toilets made possible the transportation of organic waste directly to septic systems or a municipal treatment system. Both septic and municipal treatment systems use large amounts of municipal water resources. It is widely accepted that waste treatment systems often discharge overflows of raw sewage into downstream waterways. In the past 40 years, improvements have been made to waste treatment systems by incorporating thermophilic aerobic digestion (TAD) treatment processes which makes organic waste recovery possible.

Technology exists for treatment of biosolids. Technology also exists for dry closets, which are often referred to as dry toilets. Dry closets, which normally are not connected to water supply or sewer drains, are used globally and they do have some useful features. However, dry closets do not attain the same standards the EPA requires for Class A biosolids. A lower set of standards has been set for the dry closet industry when compared to what exists for a domestic sewage treatment facility.

A set of standards exist for domestic sewage treatment technology, and are applicable to the recovery of organic waste. The U.S. EPA defines sewage sludge as "a solid, semi-solid, or liquid residue generated during the treatment of domestic sewage in a treatment works" (EPA/832-R-93-003. September 1994, p. 4). The EPA defines biosolids as "sewage sludge that has been treated and meets state and federal standards for land application" (EPA/625/R-92/013. Revised July 2003, p. 13). Thus biosolids, as defined by the phrase "for land application", are a form of recovered organic waste. When organic waste is mixed with water the unstable waste volume increases. One stage of sewage sludge treatment is a dewatering process. This volume reduction process must take place. before further treatments can occur.

Standards for Class A biosolids are discussed in EPA publication EPA/625/R-92/013 (Revised July 2003).

a. According to the EPA, "Sewage sludge is considered to be Class A if it has been treated in one of the Processes to Further Reduce Pathogens (PFRPs)" (EPA/625/R-92/013. Revised July 2003, p. 32). Composting, TAD and pasteurization are listed as processes for PFRP, each having different procedures required to achieve Class A pathogen reduction.

b. "Thermophilic aerobic digestion is a refinement of the conventional aerobic digestion processes. Because there is less sewage sludge volume and less air to carry away heat, the heat released from biological oxidation warms the sewage sludge in the digester to as high as 60° C. (140° F.). Because of the increased temperatures, this process achieves higher rates of organic solids reduction than are achieved by conventional aerobic digestion which operates at ambient air temperature. The biodegradable volatile solids content of the sewage sludge can be reduced by up to 70% in a relatively short time. The digested sewage sludge is effectively pasteurized due to the high temperatures" (EPA/625/R-92/013. Revised July 2003, p. 54). Pathogenic organisms are reduced to below detectable limits if the process is carried out at temperatures above 55° C. (131° F.).

c. "Vectors are any living organism capable of transmitting a pathogen from one organism to another either mechanically (by simply transporting the pathogen) or biologically by playing a specific role in the life cycle of the pathogen. Vectors for sewage sludge pathogens include insects, rodents and birds." Furthermore, "The term 'stability' is often used to describe sewage sludge. Although it is associated with vector attraction reduction, stability is not regulated by the Part 503 Rule. With regard to sewage sludge, stability is generally defined as the point at which food for rapid microbial activity is no longer available." (EPA/625/R-92/013. Revised July 2003, p. 58). In order to achieve reduced vector attraction, "The sewage sludge must be aerobically treated for 14 days or longer during which time the temperature must be over 40° C. (104° F.) and the average temperature higher than 45° C. (113° F.)." (EPA/625/R-92/013. Revised July 2003, p. 61).

d. "EQ biosolids are biosolids which have met the Part 503 pollutant concentration limits." (EPA/625/R-92/013. Revised July 2003, p. 20). EQ biosolids must also meet Class A requirements. U.S. EPA regulations require that all biosolids applied to the land must meet the ceiling concentrations for pollutants. The ceiling concentrations are the maximum concentration limits for 10 heavy metal pollutants in biosolids, "specifically, arsenic, cadmium, chromium, copper, lead, mercury, molybdenum, nickel, selenium, and zinc." (EPA/832-R-93-003. September 1994, p. 30). Once the requirements are met, "EQ biosolids are considered a product that is virtually unregulated for use, whether used in bulk, or sold or given away in bags or other containers." (EPA/832-R-93-003. September 1994, p. 7).

There is a large difference between domestic sewage treatment technology and dry closet technology. This is reflected in the standards set by the U.S. EPA for composting toilets requiring that "All waste materials should be disposed of in accordance with the state and local regulations." (EPA 832-F-99-066. September 1999. p. 6). There is no allowance for land application or organic waste recovery set forth within the EPA standard for composting toilets. Dry closets of the composting toilet type are generally intended to provide an alternative to a septic system or the need for a municipal treatment system. However, all waste material generated from composting toilets must be disposed of in accordance with state and local regulations. This presents a need for further treatment to achieve organic waste recovery when using a dry closet of the composting toilet type. There is a need to develop new processes and technologies for a new type of dry closet which meet the standards set by the U.S. EPA for the treatment of domestic sewage.

Most dry closets of the composting toilet type do not add water to organic waste or form a mixture of sewage sludge. When water is not added to organic waste, the dewatering process is not needed. This allows the preferred method of use to be dry aerobic digestion. Furthermore, since dry closets don't introduce heavy metal pollutants into the waste treatment process, it becomes possible to produce an aggregate result that meets requirements for EQ biosolids.

Technologies used in dry closets of the composting toilet type have some limitations. These dry closets rely on a thermophilic aerobic bacterial environment. U.S. Pat. No. 3,959,829 (PETER NORDGREN Jun. 4, 1976) describes a dry closet which uses an exhaust fan for ventilation and has "independently controllable heating means" which are used to bring the "said chamber to pasteurizing temperature". U.S. Pat. No. 4,343,051 (NILS C.PERSSON Aug. 10, 1982) describes a decomposition container with "the attainment of a rapid thermophilic decomposition process" and "a stirrer rotatable by means of an electric motor". U.S. Pat. No. 5,303,431 (LASSE JOHANSSON Apr. 19, 1994) incorporates "construction in which the outer drum is thermally insulated" within a composting toilet. Dry closet technology is limited by the need for ventilation. Ventilation is counterproductive to heat efficiency needed for thermophilic and pasteurization processes that rely on retained heat that is normally ventilated.

Urine introduced to an aerobic bacterial environment produces ammonia and causes intolerable odor conditions. Most composting toilets use continuous fan ventilation to prevent the accumulation of ammonia. Although ventilation removes waste gases and odors, it also removes heat needed for an efficient thermophilic environment. When no gas recovery process is employed, the waste gases are vented into the atmosphere. Some dry toilets divert the urine in an effort to address the problem of excessive ammonia gases being vented. Urine collection can require a large storage volume and become unpleasant to handle which is a challenge for some users. An example of a dry toilet that separates the urine is found in U.S. Pat. No. 420,332 (THOMAS W. CARRICO May 28, 1889) which describes a dry-earth closet having "a smaller perforated hopper, for the reception of the liquid excrements" anticipating that "the solids and liquid excrements will be perfectly separated".

There is a need to develop a process to stabilize and recover ammonia gases which are normally lost through ventilation. It is known that Copper(II) hydroxide can be produced from an aqueous solution of copper sulphate using sodium hydroxide or ammonia. The Copper(II) hydroxide precipitate can then be dissolved in a solution of ammonia. This process is known as Schweizer's reagent. Schweizer's reagent requires a chemical preparation stage of the transition metal. A stable metal ammine complex is formed when ammonia bonds with the transition metal. Therefore, a potential exists to develop a technology to stabilize ammonia gases based on the concept of this known process.

U.S. Patent application 2004/0023363A1 (BERNARD VAN DYK Biofiltering System for Treating Air. Feb. 5, 2004) discusses an apparatus and method "for removing odor-causing substances from the air" by using microorganisms capable of digesting the odor-causing substances. Thus, a potential exists to develop a biofiltration technology that will recover organic waste gases by incorporating a biofilter within an organic waste treatment process and device.

Dry toilets of the composting type have a limitation related to an inability to degrade lignins, the complex organic polymers which bind cellulose structure. Most composting toilets create feedstock by adding a cellulose carbon source. Some composting methods use fungal activity to degrade lignin and provide further treatment of waste material produced by composting toilets. The research paper by Deangeles, et al. "Characterization of Trapped Lignin-Degrading Microbes in Tropical Forest Soil" suggests that lignin can be transformed by microorganism produced enzymes. The authors state that "Lignin is often the most difficult portion of plant biomass to degrade, with fungi generally thought to dominate during late stage decomposition". In addition, the exploration of microbial lignin-degraders suggests "mechanisms that are different from known fungal decomposers" and "phenol oxidase and peroxidase enzyme activity was found." (http://doi.prg/10.1371/journal.pone.0019306.2011.p 1). U.S. Pat. No. 6,184,014B (TAKASHI ECHIGO Feb. 6, 2001) discusses a method to produce polyphenol oxidases from bacteria. This process needs the "optimum reaction temperature of the enzyme to be between 60 degrees C. and 80 degrees C.". Thus, the potential exists for lignin transformation by bacterial enzymes when certain conditions are met. There is a need to develop a new type of dry closet device that maintains an optimal environment for lignin transformation in a consistent and reliable manner.

Many dry closets require additional vent and drain infrastructure, which decreases their affordability. There is a need for a new type of dry closet device that can employ an organic waste treatment process while needing fewer infrastructural requirements.

Digestate is the material remaining after the anaerobic digestion of biowaste. The Northern Ireland Environment Agency (NIEA) has published a quality protocol to provide approved standards for digestate. In the UK, digestate is used as a nutrient-rich product. Digestate is directly related to the anaerobic process.

The term "biosynthate" is used in reference to the aerobic process. Biosynthate is used to denote the aggregate result of biosynthesis. Conceptually, "biosynthate refers to an aggregate measurement" of biosynthesis (Biotechnology and Bioengineering. 2013. P. 4). Biosynthate is useful to identify the material remaining after aerobic digestion of biowaste in an aerobic organic waste recovery process and device.

There exists a need for devices and processes that are an improvement to existing dry closet technology in order to decrease demand on domestic sewage treatment facilities. A new device is needed that employs a point-of-use organic waste treatment process for use in either dry closets or other larger scaled applications. A new technology is also needed to reduce greenhouse gas emissions of carbon dioxide and ammonia that come from organic waste treatment systems. Thus, there is a need for devices that separate, isolate and pasteurize organic waste solids, liquids and gases. There remains a considerable need for apparatus and methods that are self-contained and able to fully recover organic waste material in a manner consistent with standards set by the U.S. EPA for Class A (EQ) Biosolids.

All references used in these specifications are incorporated herein by reference in their entirety. Furthermore, where a definition or use of a term in a reference which is incorporated by reference herein is inconsistent or contrary to the definition of that term provided herein, the definition of that term provided herein supersedes the definition of that term in the reference.

SUMMARY

The present inventive subject matter is directed to apparatus and methods in which a thermophilic enzymatic biosynthesis (TEBS) device 50 employs a multistage aerobic synthesis transformation (MAST) treatment process 60. The TEBS device 50 may serve within a new type of dry closet for treatment of organic waste materials (solids, liquids and gases) in a manner consistent with requirements of the EPA for (EQ) biosolids. The TEBS device 50 outputs newly synthesized substances, stabilized matter and fully recovered organic material.

In a first aspect of preferred embodiments, the TEBS device 50 has a multiphase thermophilic environment chamber (MTEC) 1. The MTEC 1 accommodates several zones. Among the possibilities contemplated, a deposit zone 35 may have a disposal tray 36 serving to transport organic waste to a mixing zone 4. The disposal tray 36 comprises a collection surface 36A and a pivotal edge 36B. It is further contemplated that the deposit zone 35 may have a urine diversion channel 37.

The MTEC 1 may have the mixing zone 4 comprising a base 5 and a containment wall 6. It is contemplated that a mixing blade 20 connected to a vertical rotational shaft 23 may be centered in the mixing zone 4. The mixing blade 20 may have the functional combination of mixing, seeding and transporting. It is contemplated that the mixing blade 20 may be used for mixing organic waste solids and liquids with a carbon source and seeding the mixture with aerobic bacteria endospores. The mixing blade 20 may also transport this feedstock mixture to several zones.

The MTEC 1 may have a germination zone 7 and a multiphase germination 62. The germination zone 7 is contemplated to comprise a counter blade 8 connected to a stockpile wall segment 9 and may also have a collection-distribution area 10 for collecting feedstock from the mixing zone 4. It is contemplated that the counter blade 8 and the stockpile wall segment 9 define a sporulation area 11 located above the collection-distribution area 10.

The MTEC 1 may also have a cultivation zone 12 having a separation wall 13 connected to an accumulation wall 14 where the accumulation wall 14 is fixed to a bottom plate 15. The separation wall 13 may have an open base 16. The cultivation zone 12 may also have a collection area 17 defined by the open base 16 for collecting feedstock from the mixing zone 4. It is further contemplated that the cultivation zone 12 may have a mixing device 18 and an accumulation area 19. The accumulation area 19 extends above the separation wall 13 allowing treated solids to accumulate.

The mixing blade 20 may act to cause movement of the contents within the mixing zone 4, the collection-distribution area 10 and the collection area 17. It is further contemplated that the mixing blade 20 can have both a flat edge 21 and a shaped edge 22 which enables its functional combination. The mixing blade 20 may generate upward action within the collection-distribution area 10 and the collection area 17 when the flat edge 21 leads in rotational motion. The mixing blade 20 may generate downward action within the collection-distribution area 10 when the shaped edge 22 leads in rotational motion. It is contemplated the mixing blade 20 will perform these distinct and necessary activities when configured for bi-directional rotation.

It is contemplated that the MTEC 1 may have a pasteurization zone 24 comprising an isolation base 25 connected to an isolation wall 26. It is further contemplated that the isolation wall 26 may have a recovery outlet 26A. The mixing blade 20 passes beneath the isolation base 25 separately from the pasteurization zone 24. A platform 27 joins the isolation wall 26 associated with the pasteurization zone 24 and the separation wall 13 associated with the cultivation zone 12. It is further contemplated that the MTEC 1 has a transport blade 28 which may be fixed to the vertical rotational shaft 23. The treated solids that accumulate in the accumulation area 19 of the cultivation zone 12 may be transported across the platform 27 to the pasteurization zone 24 by the transport blade 28.

In a second aspect of preferred embodiments, the TEBS device 50 has a thermodynamic pathway 29 for directing organic waste gases. The thermodynamic pathway 29 is contemplated to have a configuration of a sloping surface 30, in which two adjacent sides of the sloping surfaces define an ascending trough 31. The ascending trough 31 may be directed to a hearth frame 32. The hearth frame 32 may have a condensation receptacle 33 and a flue passageway 34.

In a third aspect of preferred embodiments, the TEBS device 50 has a subterranean uptake chamber (SUC) 2. The SUC 2 is contemplated to comprise an uptake passageway 39 connected to a dispersion cartridge 40. Among the many different possibilities contemplated, the SUC 2 has a bottom surface 41 connected to a retention wall 42. It is further contemplated that the SUC 2 holds a plant growth medium 44 and a plant 45 where diffusing gases disperse to an uptake root structure 46 located in the plant growth medium 44.

In a fourth aspect of preferred embodiments, the TEBS device 50 may have an ammine reaction chamber (ARC) 3 and has an associated arrangement with both the MTEC 1 and the SUC 2. The ARC 3 is contemplated to comprise an oxidation surface 47 within a casing 48. The ARC 3 may be coupled to the uptake passageway 39 associated with the SUC 2 and to the flue passageway 34 associated with the MTEC 1. The ARC 3 may induce condensation of vapors, while allowing passage of gaseous vapor. The oxidation surface 47 may have reactivity to ammonia and ammonium in the vapors, which may cause a synthesis of a metal ammine complex. It is further contemplated that the ARC 3 may include a metal ammine complex drain 49 for collecting a metal ammine complex for stable, state ammonia storage.

It is further contemplated that the thermodynamic pathway 29 may have a functional respiration 64 for transport of gaseous particles from the MTEC 1 to the ARC 3 and the SUC 2.

One objective of the preferred embodiment of the invention is to allow for designed components that provide multiple functions while needing fewer parts. This may reduce production and maintenance costs and increase the reliability of the device. This makes it possible to achieve a second objective of creating a device which may have increased efficiency and reduced complexity.

Various objects, features, aspects and advantages of the present invention will become apparent from the following detailed description of preferred embodiments of the invention, along with the accompanying drawings in which like numerals represent like components.

Definition of Terms

Definition of terms used in this description and these claims:

"Multistage aerobic synthesis transformation" (MAST) treatment process refers to a multistage method for the full recovery of organic waste solids, liquids and gases. The MAST treatment process further includes a thermophilic aerobic digestion process wherein an enzymatic reaction produces newly synthesized substances including but not limited to transformed lignin, protein structures, water vapor, carbon dioxide and ammonia. The term MAST treatment process includes a HEAG process stage and further incorporates processes for recovering organic waste gases.

"HEAG process" refers to a highly efficient accelerated germination (HEAG) and includes a process of sporulation, spore seeding and repopulation of a thermophilic bacteria culture. It further relates to a state in which heat is generated, producing an accelerated thermophilic process.

The term "thermophilic" should be interpreted broadly to mean an organism (thermophile) living at a high temperature. This is exemplified by thermophilic bacteria.

"Sporulation" means asexual reproduction by the production and release of spores. As related to thermophilic bacteria, sporulation includes the formation of an endospore within a bacteria cell and occurs during inhospitable conditions.

"Multiphase germination" refers to a capacity of thermophilic bacteria spores to provide multiple phases of sporulation and repopulation of thermophilic bacteria cultures when remixed into a feedstock. The repopulation prevents a decline phase within the feedstock. Multiphase germination enables continuous culture repopulation and a thermophilic state within the feedstock, which is evidenced by a heat energy flow. The heat energy produced by multiphase germination is measurable and is directly responsible for increased energy efficiency within a thermophilic system and further directly relates to the decreased need for a supplemental heat source.

The term "germination" refers to the process whereby spores develop and begin to grow.

The term "transformed lignin" refers to the deconstruction of lignin and its dissociation from cellulose.

"Biosynthate" means the aggregate result of biosynthesis and refers to recovered organic material produced by the MAST treatment process. An example of the biosynthate includes but is not limited to transformed lignin and protein structure.

"Functional respiration" refers to a capacity of oxygen intake and waste gas exhaust and is governed by the laws of thermodynamics and relates to a convection transfer of particles. Functional respiration is measurable and is directly related to the velocity and volume of output gas vapors.

"Convection" means the process of motion involving heat transfer and upward movement of gaseous particles. The term "Convective" is an adjective form of the term convection.

"Mast's reactant" refers to the formation of a metal ammine complex and occurs when a transition metal is exposed to an organic source of ammonia. A primary reaction occurs when ammonia reacts with the transition metal to form an oxidation surface. A secondary reaction occurs when ammonia further reacts with the oxidation surface to produce a metal ammine complex. Mast's reactant facilitates recovery of ammonia gases from organic waste in the form of a metal ammine complex.

"Oxidation surface" refers to the formation of copper(II) hydroxide on the surface of the transition metal when the transition metal is copper.

"Metal ammine complex" refers to a Tetraammine copper (II) complex.

The term "disposal tray" refers to a component used for holding and carrying solid or semi-solid matter.

The term "feedstock" refers to raw material that provides ingredients necessary for the support of a thriving thermophilic bacteria culture population. The ingredients may comprise a mixture of organic waste, a carbon source and a bacterial culture.

The term "stockpile" means a reserve supply accumulated for future use.

The term "multiphase refers to more than one phase interacting simultaneously, specifically, in the context of a state of multiphase flow.

The term "collection" means the process of gathering materials together for a particular purpose.

The term "distribution" means the process of spreading something over an area.

The term "substance" refers to matter which has uniform properties.

The term "stability" refers to the ability to stay in the same state.

The term "subterranean" refers to being located or operating under the surface soil or other soil-like materials.

The term "uptake" means the action of absorbing and incorporating substances into an inorganic or organic structure.

Glossary of acronyms and abbreviations used in this description:
ARC ammine reaction chamber
HEAG highly efficient accelerated germination
MAST multistage aerobic synthesis transformation
MTEC multiphase thermophilic environment chamber
ROWG recovery of organic waste gases
SUC subterranean uptake chamber
TEBS thermophilic enzymatic biosynthesis

BRIEF DESCRIPTION OF DRAWINGS

FIG. 1A-1C show perspective, front, and side views, respectively, of a housing structure 52 for a TEBS device 50.

BEST MODE FOR CARRYING OUT THE INVENTION

General Overview

Persons of ordinary skill in the art will realize that the following description of the present invention is illustrative only and not in any way limiting. Other embodiments of the invention will readily suggest themselves to such skilled persons. The following discussion provides many example embodiments of the inventive subject matter. Although each embodiment represents a single combination of the inventive elements, the inventive subject matter is considered to include all possible combinations of the disclosed elements.

In a preferred embodiment depicted in FIGS. 1A-1C, a thermophilic enzymatic biosynthesis (TEBS) device 50 includes a housing structure 52 which provides a decorative and attractive enclosure for the device components as well as providing a weight stability contour for the user. All of the components of the TEBS device 50 are incorporated within the housing structure 52; thus, it is a point of use device designed for full recovery of organic waste. This embodiment is particularly useful for a new type of dry closet, because it will satisfy certain stringent EPA requirements for organic waste recovery.

Figure 1D:
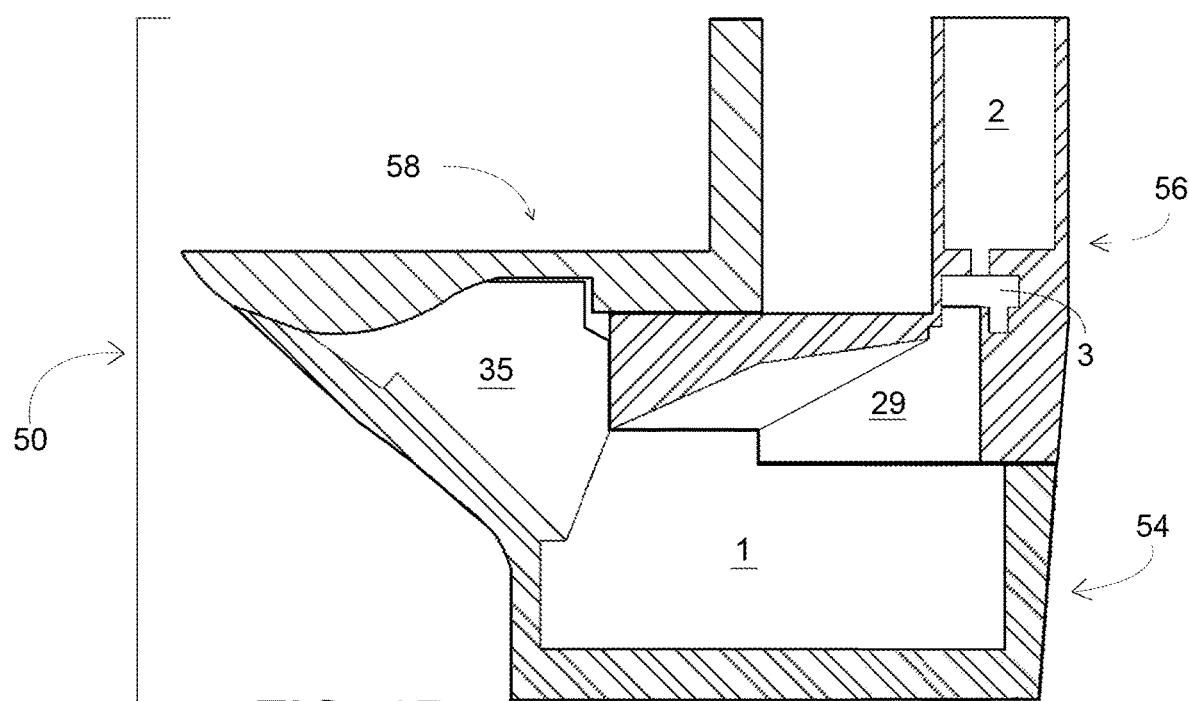
FIG. 1D is a sectional side view of an embodiment of the TEBS device 50.
Figure 1E:
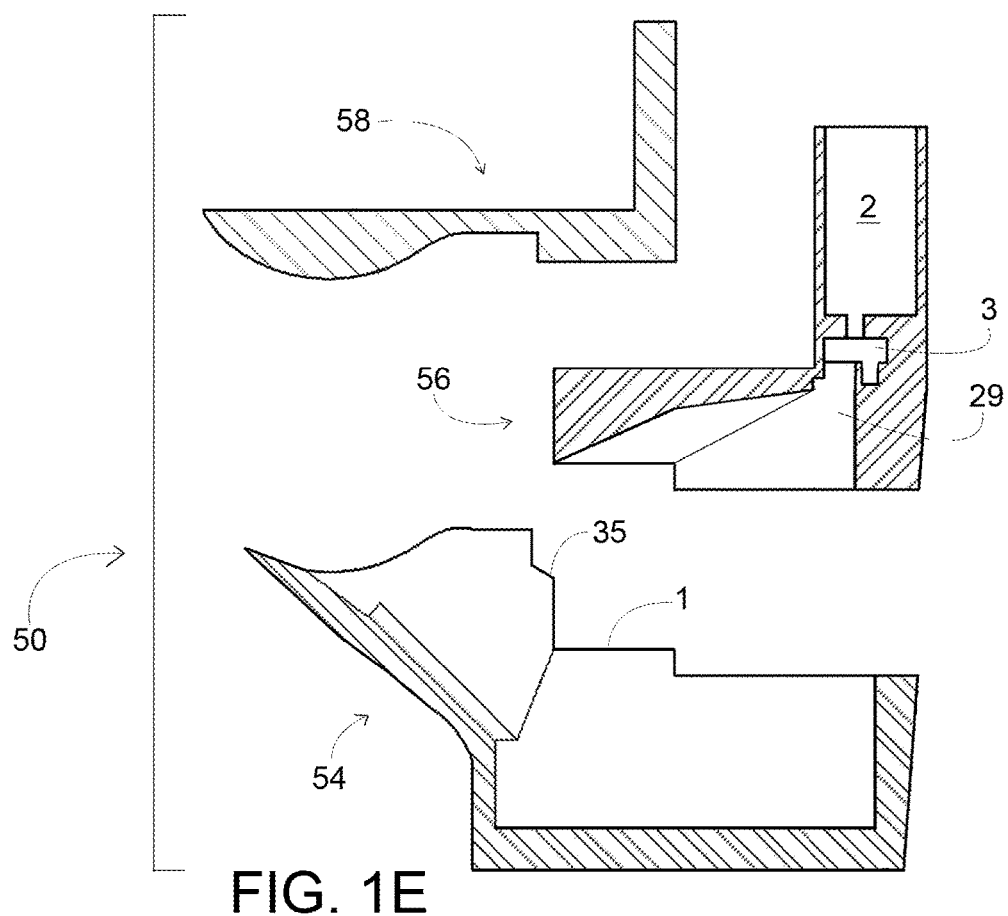
FIG. 1E is an exploded view of the embodiment of FIG. 1D.

In a preferred embodiment depicted in FIGS. 1D and 1E, the housing structure 52 includes three subassemblies.

Figure 3A:
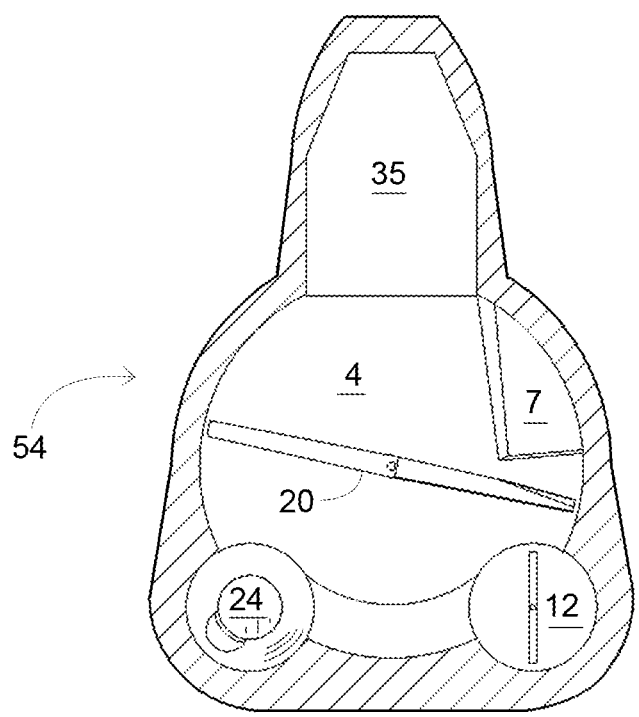
FIGS. 3A and 3B are a top view and perspective cutaway view, respectively, of an embodiment of a lower housing assembly 54 according to the inventive subject matter.
Figure 3B:
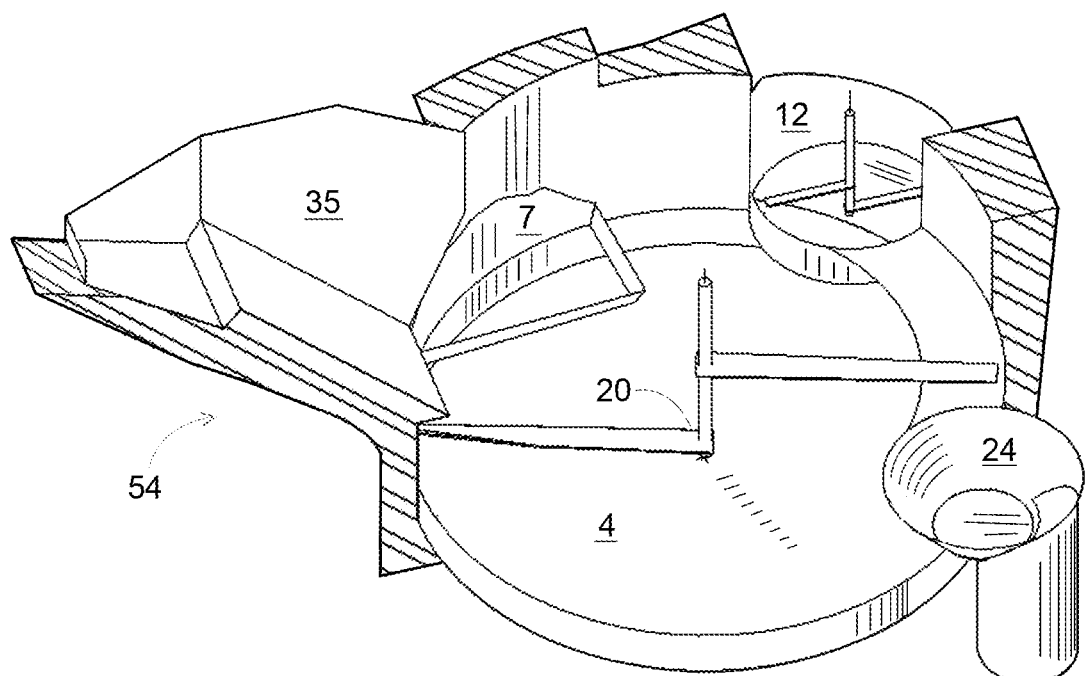
Figure 4A:
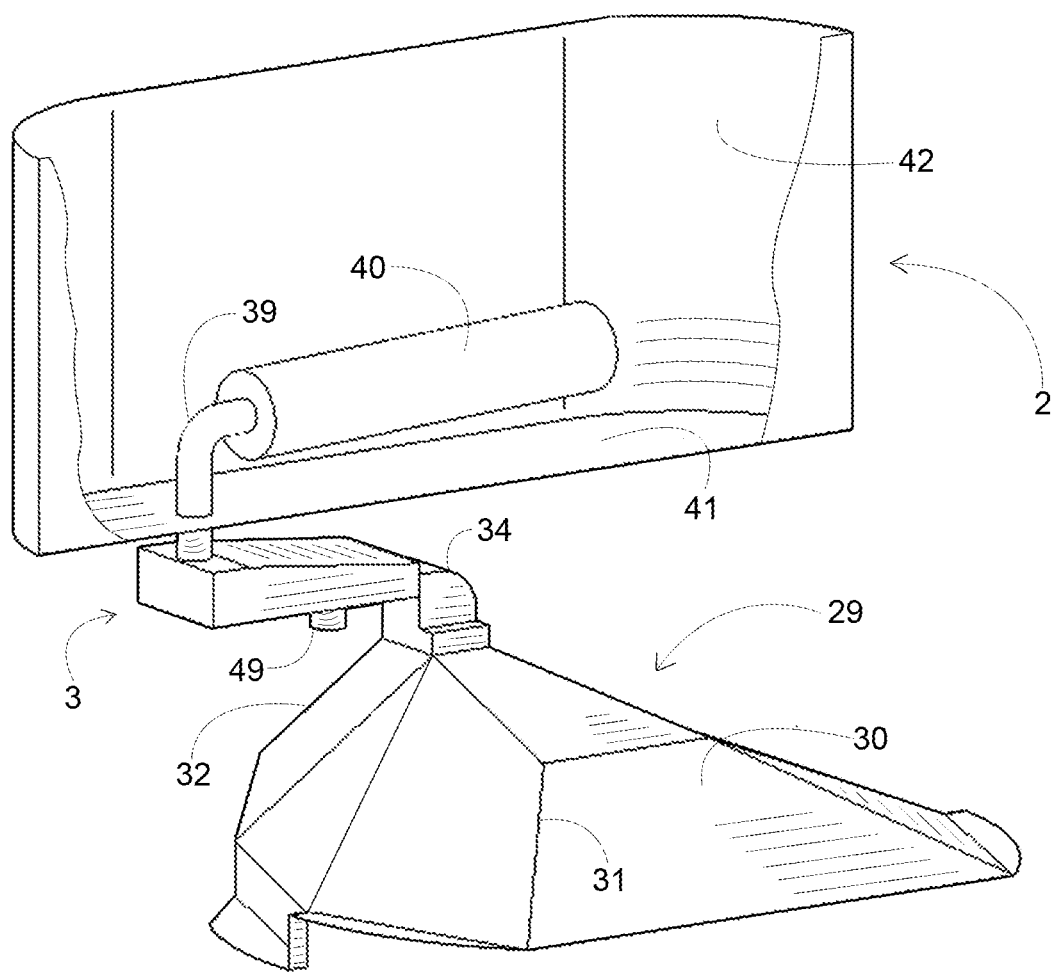
FIG. 4A is a cutaway perspective view of structures within an upper housing assembly 56 according to an embodiment of the inventive subject matter.

The housing structure 52 can be divided into two major subassembly components: a lower housing subassembly 54 and an upper housing subassembly 56. The major structures contained within the lower housing subassembly 54 include a multiphase thermophilic environment chamber (MTEC) 1 and a deposit zone 35 as depicted in FIG. 1E. Details of the lower housing subassembly 54 are depicted in FIGS. 3A and 3B. The major structures contained within the upper housing subassembly 56 include a thermodynamic pathway 29, a subterranean uptake chamber (SUC) 2 and an ammine reaction chamber (ARC) 3 as depicted in FIG. 1E. Details of the structures within the upper housing subassembly 56 are depicted in FIG. 4A.

The third subassembly of the housing structure 52 is a seat and back assembly 58 which provides user access to control components. The seat and back assembly 58 are depicted in FIG. 1E.

Figure 5:
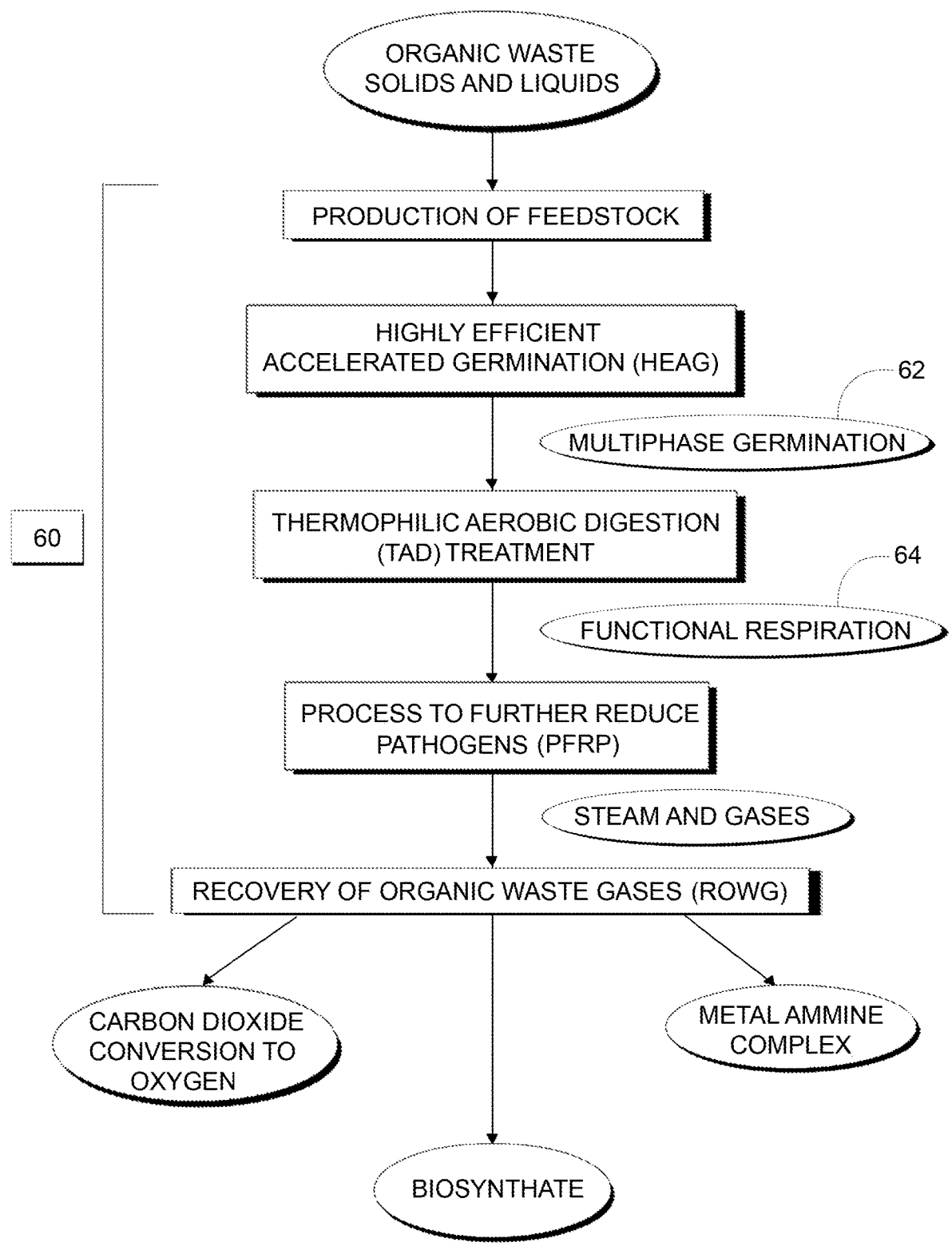
FIG. 5 is a schematic of the MAST treatment process 60 employed by the TEBS device 50 according to the inventive subject matter.

The TEBS device 50 employs a multistage aerobic synthesis transformation (MAST) treatment process 60 which can be divided into five stages of treatment as depicted in FIG. 5.

A first stage of treatment, production of feedstock, includes mixing and size reduction. A second stage of treatment, highly efficient accelerated germination (HEAG) process, includes sporulation, endospore seeding and repopulation. A third stage of treatment, thermophilic aerobic digestion (TAD), provides a reduction of the biodegradable volatile solids content. A fourth stage of treatment, process to further reduce pathogens (PFRP), provides pasteurization essential for vector attraction reduction and stability. A fifth stage of treatment, recovery of organic waste gases (ROWG), includes ammonia stabilization and carbon dioxide conversion.

Figure 2A:
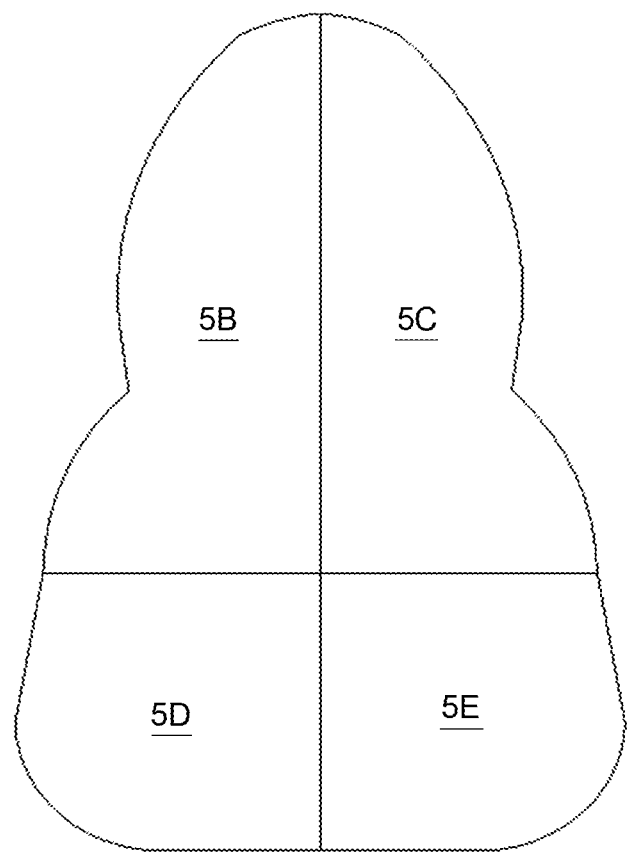
FIG. 2A is a top view of the four quadrants.
Figure 2B:
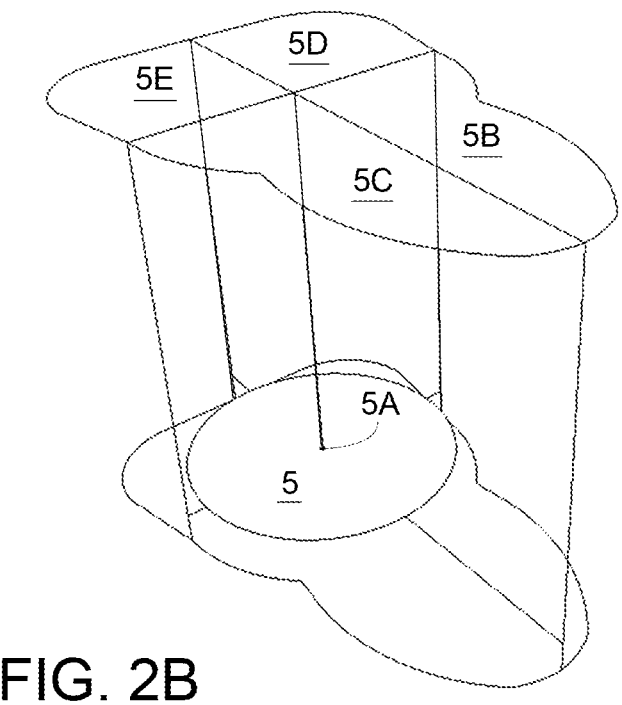
FIG. 2B is a perspective view of the four quadrants.

Four quadrants are depicted in FIGS. 2A and 2B.

The four quadrants serve to locate the structural components within the TEBS device 50 according to a preferred embodiment of the inventive subject matter.

A base 5 is centrally located at the bottom of the MTEC 1 and has a radius anchored at a center point 5A. The center point 5A is used to establish the axes of four quadrant regions: a left-front quadrant 5B, a right-front quadrant 5C, a left-rear quadrant 5D and a right-rear quadrant 5E. The four quadrants provide a coordinate orientation, which is useful for locating positions of zones and components in three dimensions.

DETAILED DESCRIPTION

Figure 3C:
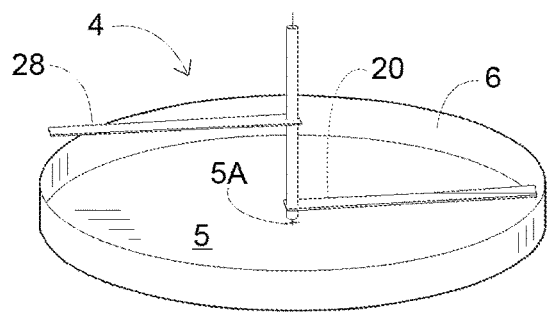
FIG. 3C is a perspective view of a mixing zone 4 according to an embodiment of the inventive subject matter.
Figure 3E:
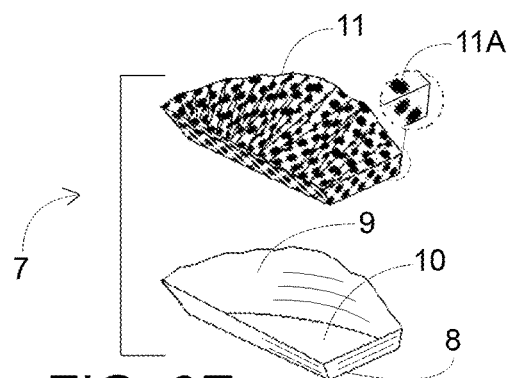
FIGS. 3E and 3F are an exploded view and a perspective view, respectively, of a germination zone 7 according to an embodiment of the inventive subject matter.
Figure 3G:
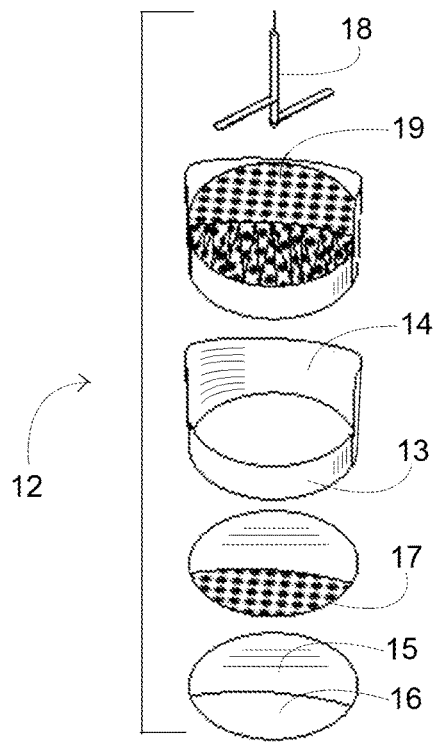
FIGS. 3G and 3H are an exploded view and a perspective, respectively, of a cultivation zone 12 according to an embodiment of the inventive subject matter.
Figure 3F:
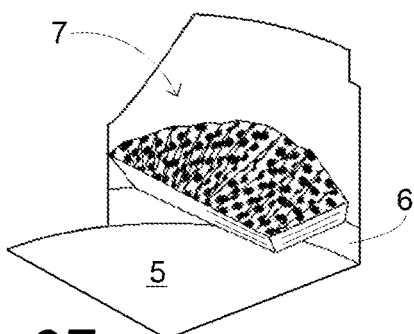
Figure 3J:
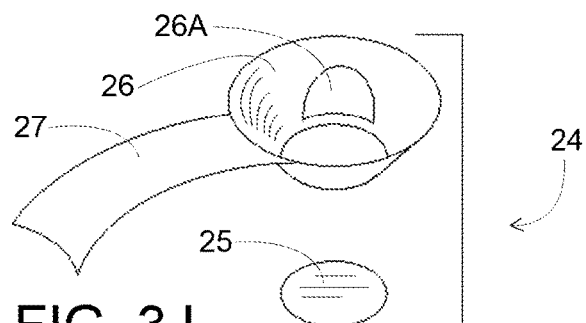
FIGS. 3J and 3K are an exploded view and a perspective view, respectively, of a pasteurization zone 24 according to an embodiment of the inventive subject matter.
Figure 3H:
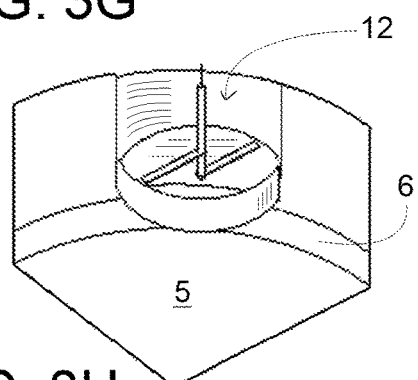
Figure 3K:
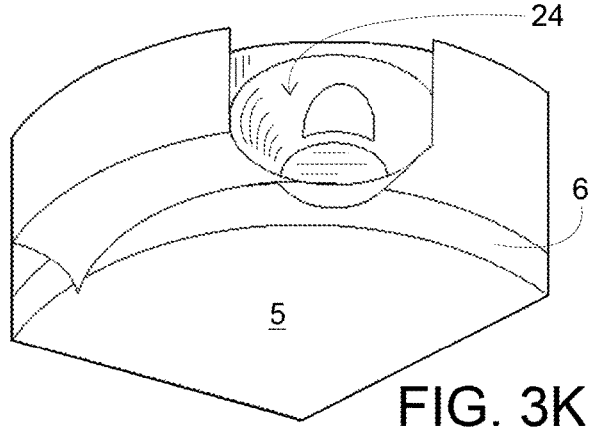
Figure 3D:
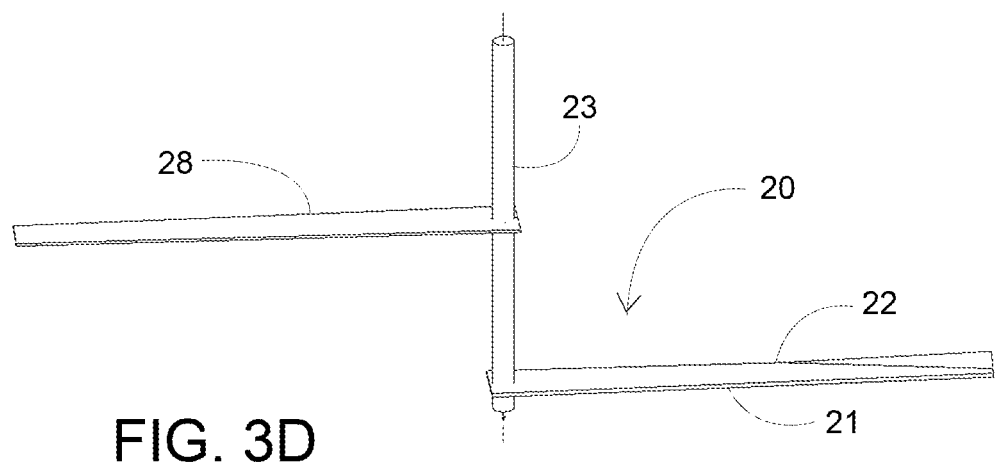
FIG. 3D is a perspective detail view of a mixing structure as seen in FIG. 3C.
Figure 3L:
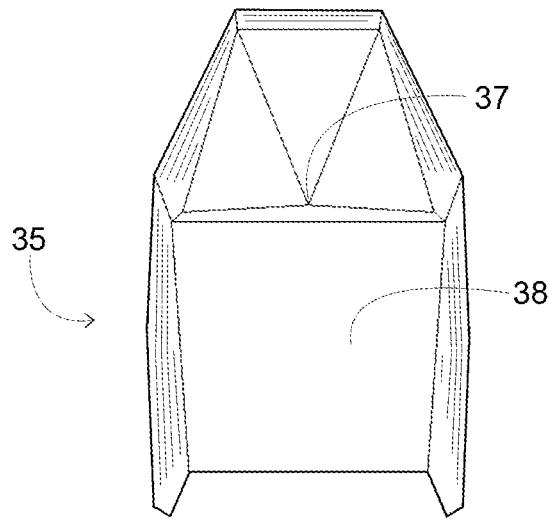
FIG. 3L is a top perspective view of a deposit zone 35 according to an embodiment of the inventive subject matter.
Figure 3M:
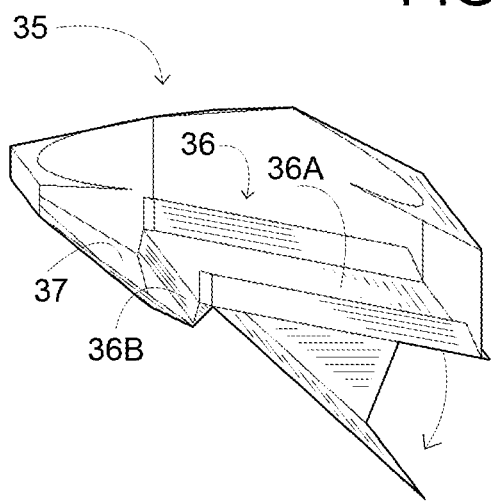
FIG. 3M is a cutaway perspective view of a disposal tray 36, of the deposit zone 35, in a closed position according to the inventive subject matter.
Figure 3N:
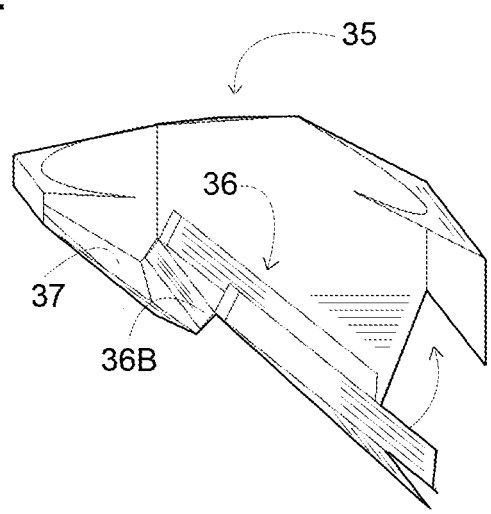
FIG. 3N is a cutaway perspective view of a disposal tray 36, of the deposit zone 35, in an open position according to the inventive subject matter.

The deposit zone 35 is depicted in FIGS. 3L-3N according to a preferred embodiment.

In a preferred embodiment, the deposit zone 35, located in the front quadrants 5B and 5C, and having a chute 38 and a disposal tray 36, is configured to allow reception of organic waste and the deposit of said organic waste into a mixing zone 4. The disposal tray 36 is positioned in front of and above the mixing zone 4. The chute 38 is shaped to accommodate the disposal tray 36 which is generally a rectangular shape with walls formed on two opposite sides of a collection surface 36A. A pivotal edge 36B, located on the front side of the disposal tray 36, allows removable functionality within the chute 38. Advantageously, the disposal tray 36, creates a seal within the chute 38 when resting in a horizontal position. One example of allowing the disposal tray 36 to be removably functional within the chute 38 is positioning the pivotal edge 36B to rest in a urine diversion channel 37. The deposit zone 35 and related components are formed of materials and fabrication procedures consistent with those used for other MTEC 1 components.

An efficient treatment process for organic waste liquids and solids is utilized within the MTEC 1.

The lower housing subassembly 54 contains the MTEC 1, which has several zones is depicted in FIGS. 3A and 3B.

Each zone is designed to provide a treatment stage essential to the MAST treatment process 60. These zones are designed to allow interaction with a mixing blade 20. The interaction of the mixing blade 20 with the zones is essential for creating a flow of organic waste and feedstock that results in fully recovered organic aggregate. The MAST treatment process 60, employed within the TEBS device 50 produces a biosynthate aggregate. The biosynthate aggregate has many characteristics of nutrient-rich soils found in nature. The biosynthate produced by the TEBS device 50 has defining characteristics when mixed with water. The biosynthate is insoluble and produces no offensive odor or methane when mixed with water. This is not true for the organic waste before treatment within the preferred embodiment of the invention.

The mixing zone 4 facilitates feedstock production.

In a preferred embodiment as depicted in FIG. 3C, the mixing zone 4 comprises the base 5, a containment wall 6 and the mixing blade 20. The mixing zone 4 is configured to facilitate the first stage treatment of organic waste solids, liquids and gases. By combining the organic waste with carbon sources and a bacteria culture, organic waste is transformed into a resource essential for production of feedstock.

The base 5 is generally a flat spherical surface, having a diameter useful to calculate the dimensional area of the mixing zone 4. This area, along with the containment wall 6 dimensional height, is useful to determine the cubic capacity of said mixing zone 4. The base 5 diameter is further used as a parameter, where associated components have dimensions expressed by a ratio relating to the base 5 diameter. For example, the length of component A is determined in relationship to the base 5 diameter using a 1:2 ratio.

The containment wall 6, which has no outlet, is joined to the base 5 perimeter to form a liquid accumulation area. The containment wall 6 is joined to the base 5 perimeter in a fixed position by suitable means such as welding or solder fabrication, although embodiments may utilize other forms of joining known to persons skilled in the arts. The base 5, the containment wall 6 and related MTEC 1 components are formed of a corrosion-resistant rigid material, preferably stainless-steel sheet metal; although other embodiments may utilize materials of composites, ceramic coating, glass or other corrosion-resistant materials known to persons skilled in manufacture of the art.

Persons skilled in the art will realize that the cubic capacity of the mixing zone 4 and the containment wall 6 height will depend on many factors including general device application and the type of organic waste to be treated and recovered. In one non-limiting example, the containment wall height is approximately two inches and the mixing zone 4 capacity is 508 cubic inches. The contemplated containment wall height may be in the range of one to three inches for the preferred embodiment, although other embodiments may utilize heights greater than three inches.

A carbon source, also known as a bulking agent, can include material such as sawdust, coconut husk, or peat moss. Persons of ordinary skill in the art will readily appreciate that other materials can be used as a carbon source for mixing with organic waste in accordance with the teachings of the present invention.

Details of the mixing blade 20 are depicted in FIG. 3D.

In a preferred embodiment, the mixing blade 20 is designed to facilitate a multi-functionality of one moving part interacting with several stationary components in order to provide oxygenation, size reduction of waste matter and distribution of the feedstock.

The mixing blade 20 preferably has a flat edge 21 and a shaped edge 22, where the flat edge 21 defines a horizontal section of the blade surface and the shaped edge 22 is defined by an upward bend in the blade surface to create a sloping portion of the blade. The mixing blade generates upward action upon the feedstock when the flat edge 21 leads in motion. The mixing blade generates downward action upon the feedstock when the shaped edge 22 leads in rotational motion. The mixing blade 20 moves in a rotational path around the center point 5A and extends outwardly towards the containment wall 6 in such a way that acceptable clearances exist between the mixing blade and the stationary components. The stationary components include but are not limited to the base 5, the containment wall 6, a counter blade 8, a separation wall 13 and an isolation base 25.

The mixing blade 20 is connected to a vertical rotational shaft 23 which has a rotational coupling mounted to the base 5 in a conventional manner, such as a sleeve bushing mounted to a standard pin fixed to the center point 5A. Examples of suitable pin types include bolts, rod stocks and studs. The mixing blade 20 is fabricated of a conventional corrosion-resistant material type, preferred to be a stainless steel metal such as a rod or bar stock and fabricated according to manufacturing methods common to those skilled in the art, although other embodiments may utilize optional materials used in different manufacturing sectors.

A non-limiting example of an acceptable clearance for the preferred mixing blade 20 is a distance of about 0.25 inch up to about one inch, although other embodiments may utilize a distance greater than one inch. Persons skilled in the art will realize that the specific clearance used will depend on many factors including the types of organic waste matter to be mixed, the desired size reduction and the maximum allowable blade resistance for a given embodiment.

A germination zone 7 efficiently utilizes a multiphase germination 62. Details of the germination zone 7 are depicted in FIGS. 3E and 3F.

In a preferred embodiment, the germination zone 7 has said counter blade 8, a stockpile wall segment 9, a collection-distribution area 10 and a sporulation area 11. The germination zone 7, which utilizes the multiphase germination 62, is configured to facilitate a second stage of treatment (HEAG process).

The germination zone 7 is generally a triangular prism shape. The counter blade 8 has a union of two straight bars sharing an endpoint to form an angle (as depicted in FIG. 3E) and is coupled to the stockpile wall segment 9, defining a configuration for the collection-distribution area 10. The counter blade 8 is positioned in the right-front quadrant 5C extending in either a horizontal or a sloping orientation and has an elevation that provides communication with the mixing zone 4. The counter blade 8 position is advantageous for interaction with the mixing blade 20. Feedstock moves through the collection-distribution area 10 as the mixing blade 20 interacts with the counter blade 8. The interaction of the mixing blade 20 with the counter blade 8 provides seeding of endospores, which is essential for creating conditions favorable for thermophilic bacteria repopulation, thus preventing a decline phase within the feedstock. Some embodiments may employ the counter blade 8 in the left-front quadrant 5B or a combination of positions not limited to the front quadrants 5B and 5C. The counter blade 8 is removably fixed to the stockpile wall segment 9 using conventional hardware such as screws or bolts to provide a structural cantilever.

The counter blade 8 is fabricated from a flat bar or a round bar, preferably of a stainless steel material. Other embodiments may utilize various corrosion-resistant materials. The stockpile wall segment 9 is a section of the MTEC 1 sidewall that is designed for mounting the counter blade 8 and accommodating feedstock, both being essential for the sporulation area 11. The design of the germination zone 7 enables a high population of thermophilic bacteria cultures 11A within the sporulation area 11, thus enabling the multiphase germination 62.

Each time the mixing blade interacts with the counter blade 8 to generate downward action upon the feedstock, the high population of thermophilic bacteria cultures 11A is distributed throughout the mixing zone 4. This action initiates a new phase of germination because thermophilic bacteria spores are added to the feedstock being produced in the mixing zone 4. The multiphase germination 62 is amplified in the mixing zone, and perpetuates a thermophilic state, as evidenced by a heat energy flow. The multiphase germination 62 is structured within the feedstock and is formed of thermophilic endospores and the high population of thermophilic bacteria cultures 11A. In a preferred embodiment, the multiphase germination 62 is accommodated by and located in the sporulation area 11, the mixing zone 4 and a cultivation zone 12. The shape of the multiphase germination 62 is generally defined but not limited by these areas. The preferred thermophilic endospore-producing bacteria are found in common soils and the human digestive system.

Persons skilled in the art will appreciate that different types of thermophilic bacteria culture are suitable for use in constructing the multiphase germination 62.

Said cultivation zone 12 provides a thermophilic aerobic digestion (TAD) process. Details of the cultivation zone 12 are depicted in FIGS. 3G and 3H.

In a preferred embodiment, the cultivation zone 12 comprises a collection area 17, an accumulation area 19 and a mixing device 18. The cultivation zone 12 is designed to enable feedstock digestion which is essential for the reduction of biodegradable solids content of organic waste and the production of newly synthesized substances. Thus, the cultivation zone 12 is configured to facilitate the MAST treatment process 60 (third stage TAD) and production of biosynthate.

The cultivation zone 12 is generally a cylindrical shape and includes said separation wall 13, an accumulation wall 14, a base plate 15 and an open base 16. The bottom plate 15 is generally a flat surface. The bottom plate 15 together with the open base 16 forms a circumference having a diameter and a center axis point. The bottom plate 15 and the separation wall 13 are separately joined to the accumulation wall 14 as depicted in FIG. 3G. The bottom edge of the separation wall 13 defines the open base 16. The open base 16 allows collection and accumulation of feedstock within the cultivation zone 12. The bottom plate 15 is joined to the accumulation wall 14 in a conventional fashion such as metal or composite fabrication.

The cultivation zone 12 is positioned in the right-rear quadrant 5E with the bottom plate 15 having a horizontal orientation, which is preferably at an elevation equal to or below the counter blade 8. This configuration allows the mixing blade 20 to interact with the open base 16, generating an uplift of feedstock into the cultivation zone 12.

The mixing device 18 has at least one mixing arm and is configured to provide oxygenation and evaporation, both of which are essential for thermophilic aerobic digestion (TAD) treatment. The mixing arms may be straight or curved and are configured to prevent compaction of the newly synthesized substances. Persons skilled in the art will realize that the type of mixing device 18 used will depend on many factors including the level of automation and energy efficiency desired. In one non-limiting example, the cultivation zone diameter is determined in relationship to the base 5 diameter using a 1:3 ratio.

The cultivation zone 12 and related components are formed of conventional materials consistent with the other MTEC 1 components. Conventional joints are used such as a welding or solder fabrication, although embodiments may utilize other forms of joining including pressed and sealed joints or other methods preferred by a person skilled in fabrication processes.

A pasteurization zone 24 provides a process to further reduce pathogens (PFRP). Details of the pasteurization zone 24 are depicted in FIGS. 3J and 3K.

In a preferred embodiment, the pasteurization zone 24 comprises said isolation base 25, an isolation wall 26 and a recovery outlet 26A. The pasteurization zone 24 is configured to provide isolation of biosynthate, which is essential for vector attraction reduction and allows biosynthate to reach a point of stability.

The isolation base 25 is joined and sealed to the isolation wall 26 in a fixed position to prevent contamination of the biosynthate. Thus, the pasteurization zone 24 is designed to facilitate the fourth stage of the MAST treatment process 60, which is a process to further reduce pathogens (PFRP).

The pasteurization zone 24 is positioned in the left-rear quadrant 5D, wherein the isolation base 25 has an elevation similar to the counter blade 8. The pasteurization zone 24 also comprises a platform 27 that extends horizontally from the isolation wall 26 to the separation wall 13. The platform 27 provides association between the cultivation zone 12 and the pasteurization zone 24. The biosynthate in the accumulation area 19 is transported across the platform 27 by a transport blade 28. The transport blade 28, as depicted in FIG. 3D, is fixed to the vertical rotational shaft 23 and positioned to allow an appropriate clearance with the platform 27. The transport blade 28 facilitates movement of biosynthate from the cultivation zone 12 into the pasteurization zone 24.

The isolation wall 26 is generally of a conical shape, forming a funnel-like collection area for pasteurization of biosynthate. The funnel shape of the pasteurization zone 24 allows movement of the biosynthate towards the recovery outlet 26A. The recovery outlet 26A is located on the isolation wall 26.

The pasteurization zone 24 and related components are fabricated of conventional materials and fabrication methods consistent with the other MTEC 1 components. It has been contemplated that a conventional heat source (not shown) utilized for pasteurization could include but is not limited to an electric heat element or a hot water source such as a boiler or solar panel.

The upper housing assembly 56 utilizes an efficient ROWG Process. Details of the upper housing assembly 56 are depicted in FIG. 4A.

Figure 4B:
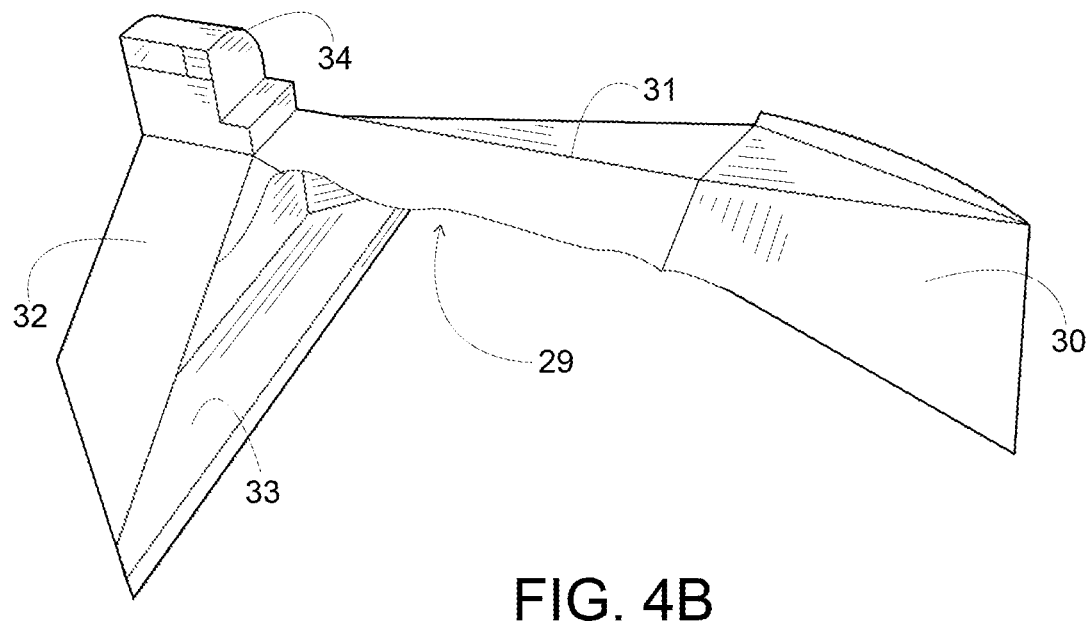
FIG. 4B is a cutaway perspective view of a thermodynamic pathway 29 according to an embodiment of the inventive subject matter.

The thermodynamic pathway 29, as depicted in FIG. 4B utilizes a functional respiration 64.

In a preferred embodiment, the thermodynamic pathway 29 has a sloping surface 30 and an ascending trough 31, and is designed to facilitate a fifth stage of the MAST treatment process 60. By forming straight lines from lowest elevation to the highest elevation for the intersections of the sloping surface 30, the ascending trough 31 is defined. This creates a pathway for rising gases and a state of thermodynamic advantage which together establish the functional respiration 64. The functional respiration 64 has a capacity to produce an efficient flow of organic waste gases for meeting system oxygen demands and removing waste gases. The inclusion and use of the functional respiration 64 eliminates the need for continuous ventilation by a fan device (not shown) and creates efficient heat retention within the TEBS device 50. The thermodynamic pathway 29 is generally irregular in shape having a circumference defined by the top edge of the MTEC 1 side walls, so that rising gases are directed from the MTEC 1 to the ARC 3. The thermodynamic pathway 29 has a hearth frame 32 which is positioned at the highest possible elevation within the MTEC 1 in the left and right rear quadrants 5D and 5E. The positioning of the hearth frame 32 provides an area for rising gases to accumulate. The hearth frame 32 has a condensation receptacle 33 extending horizontally across the hearth frame 32 base area and facilitates recovery of water vapor. A flue passageway 34 is joined and fixed to the top of the hearth frame 32. The thermodynamic pathway 29 assembly and related components are fabricated of conventional materials and fabrication methods consistent with the other MTEC 1 components. In a preferred embodiment, the functional respiration 64 is accommodated by and located in the thermodynamic pathway 29. The functional respiration 64 comprises expanding and rising gases. The shape of the functional respiration 64 is generally defined by the surface area of the thermodynamic pathway 29. An example of preferred gaseous structures used for constructing the functional respiration 64 can be ammonia, carbon dioxide, hydrogen and oxygen.

Figure 4C:
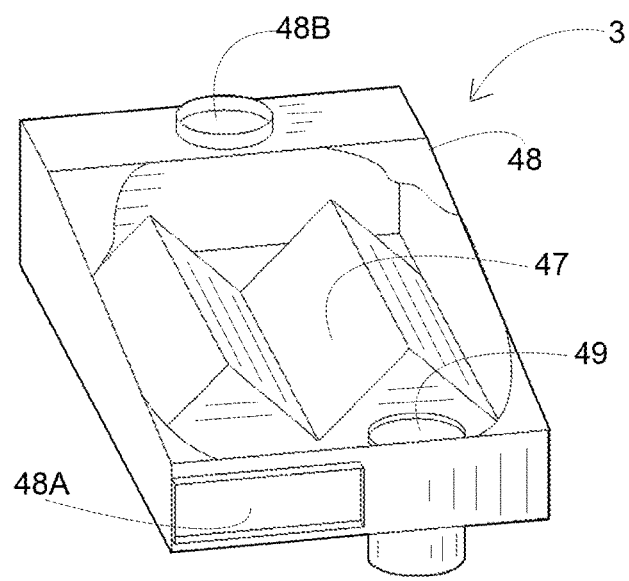
FIG. 4C is a cutaway perspective view of an ammine reaction chamber (ARC) 3 according to an embodiment of the inventive subject matter.

Details of the ammine reaction chamber (ARC) 3 are depicted in FIG. 4C.

In a preferred embodiment, the ARC 3 has a casing 48, an oxidation surface 47 and a metal ammine complex drain 49 and is configured to facilitate ROWG, the fifth stage of the MAST treatment process.

The casing 48 has a first orifice coupling 48A and a second orifice coupling 48B and is generally a rectangular box shape with dimensions larger than the orifice couplings. This design allows a turbulent airstream of condensing vapors within the ARC 3. The ARC 3 provides an optimal environment for the oxidization surface 47. Other embodiments may utilize alternate shapes to accomplish the same function.

The first orifice coupling 48A is joined to the flue passageway 34 and the second orifice coupling 48B is joined to an uptake passageway 39. Both couplings are removably fixed to form a seal coupling in a conventional fashion using a suitable material such as a silicone sealant. Other embodiments may employ a seal joint using a frictional gasket, a compression fitting or an O-ring type joint. The ARC 3 is positioned in the right-rear quadrant 5E and extends diagonally at an elevation that makes interaction possible with both the MTEC 1 and the SUC 3.

The oxidation surface 47 is an ammine transition metal. The preferred ammine transition metal, copper, is used to generate stable-state ammonia. When gaseous ammonia is converted into a non-gaseous state, it advantageously inhibits obnoxious odors normally associated with ammonia. The casing 48 is fabricated from a conventional corrosion-resistant material, preferably stainless steel; although other embodiments may be formed using composite materials.

Persons of ordinary skill in the art will further appreciate that because the MTEC 1 utilizes a functional respiration 64, a source of ammonia gas becomes available to the ARC 3 and a useful set of conditions exist for Mast's reactant, an organic ammine copper reaction. Mast's reactant provides recovery of ammonia gases from organic waste in the form of a metal ammine complex.

Figure 4D:
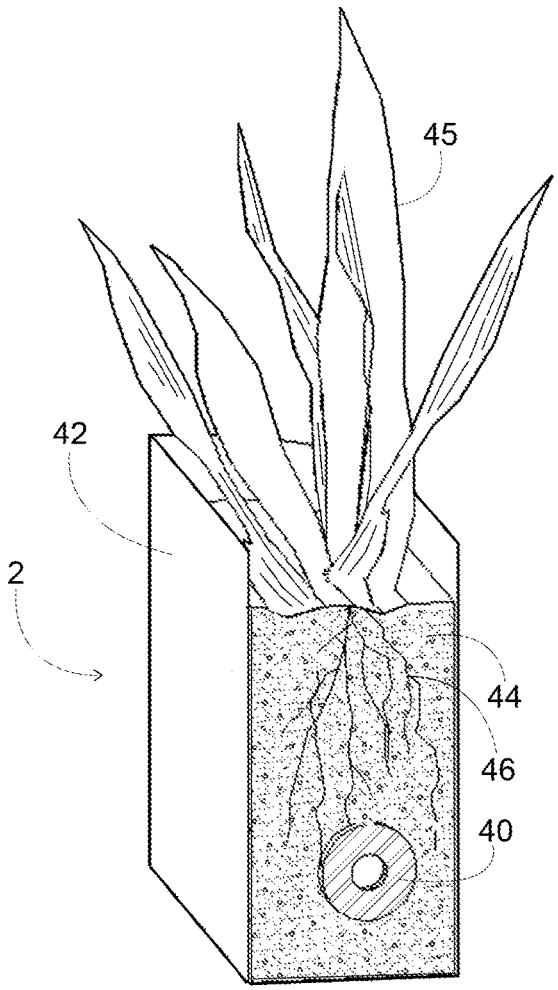
FIG. 4D is a cutaway perspective view of a subterranean uptake chamber (SUC) 2 according to an embodiment of the inventive subject matter.

The subterranean uptake chamber (SUC) 2, as depicted in FIG. 4A and FIG. 4D, provides treatment of unrecovered organic waste gases transferred from the ARC 3.

In a preferred embodiment, the SUC 2 comprises the uptake passageway 39, a dispersion cartridge 40 and an uptake root structure 46. The SUC 2 is designed to facilitate the fifth stage ROWG treatment. The inclusion and use of the SUC 2 is necessary to eliminate the need for direct outdoor ventilation of the TEBS device 50.

In a preferred embodiment, the SUC 2 is generally a three-dimensional shape defined by a bottom surface 41 with a retention wall 42 that extends from the bottom surface 41 upwards. The SUC 3 accommodates a plant growth medium 44, a plant 45 and the uptake root structure 46 which act together as a biological chamber. One example of plants suitable for use in the SUC 3 is *Spathiphyllum Wallisii*, a commonplace household air filtering plant. The biological components of the SUC 3 are essential to the retention and consumption of sulfur and conversion of carbon dioxide to oxygen. The SUC 2 is preferably positioned in the rear-quadrants 5D and 5E above the MTEC 1.

The uptake passageway 39 is bonded to the retention wall 42 in a fixed position and extends into the SUC 3. The dispersion cartridge 40 is coupled to the uptake passageway 39 in a removably fixed manner, such as a frictional insert.

Untreated gases that pass through the uptake passageway 39 are allowed to diffuse from the dispersion cartridge 40 into the plant growth medium 44. The conditions needed for a subterranean uptake process are met and diffusing gases disperse to the uptake root structure 46 located in the plant growth medium 44. The dispersion cartridge 40 can be a generic carbon filter cartridge with a pass-through design and allows for low cost and convenient replacement.

The SUC 3 and related components are fabricated from a conventional corrosion-resistant material, preferably stainless steel; although other embodiments may be formed using composite materials. Other embodiments may be fabricated by a molded manufacture process using associated materials.

The preferred embodiments can be divided into three subassemblies, however it is contemplated that alternative combinations of the three subassemblies can comprise different configured embodiments. For example, the housing can comprise individual subassemblies or a combination of two different subassemblies. It is further contemplated that alternative embodiments may include a plurality of subassemblies in different possible configurations. For example, an alternative embodiment may have a second MTEC 1 subassembly receiving diverted urine to increase the liquid waste capacity of the device. It is further contemplated that utilizing a plurality of the ARC 3 subassemblies to increase stable state ammonia storage capacity maximizes the energy application of recovered organic waste gases.

As used herein and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

While embodiments and applications of this invention have been shown and described, it should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context.

INDUSTRIAL APPLICABILITY

A thermophilic enzymatic biosynthesis (TEBS) device 50 as described in the claims has application to a new process for attaining the same standards set by the U.S. EPA for Class A exceptional quality (EQ) biosolids The TEBS device 50, as described in the claims, relates to technology for transforming organic wastes into a biosynthate aggregate. Said device, employs a point-of-use that incorporates the technological benefits of highly efficient accelerated germination, recovery of organic waste gases, biofiltration and Mast's reactant. Mast's reactant is an organic ammine reaction allowing recovery of ammonia in the form of an ammine solid.

The TEBS device 50, as described in the claims, provides new innovation for the industrial application of organic waste recovery.

CITATION LIST

Patent Literature

U.S. Pat. No. 3,959,829 (PETER NORDGREN) 1 Jun. 1976; Column 2, lines 2-4; Column 3, lines 26, 52-54; discusses a pasteurization, heat control, and ventilation by means of an exhaust fan.

U.S. Pat. No. 4,343,051 (NILS C. PERSSON) 10 Aug. 1982; Abstract, discusses thermophilic decomposition and stirring means by an electric motor.

U.S. Pat. No. 5,303,431 (LASSE JOHANSSON) 19 Apr. 1994; Column 4, lines 37, 38; discusses a thermally insulated drum.

U.S. Pat. No. 420,332 (THOMAS W. CARRICO) 28 May 1889; Page 1, lines 87-91; Page 2, lines 24-27; discusses separation of solid and liquid excrements.

U.S. Pat. No. 6,184,014B (TAKASHI ECHIGO) 2 Jun. 200; Abstract; discusses a method to produce polyphenol oxidase to be produced by bacteria.

US 2004/0023363A1 (BERNARD VAN DYK) 2 May 2004; Abstract; discusses biofiltration for treating air.

Non-Patent Literature

U.S.EPA. A Plain English Guide to the EPA Part 503 Biosolids Rule. *EPA/832-R-93-003*. September 1994, p. 4.

U.S.EPA. Environmental Regulations and Technology Control of Pathogens and Vector Attraction in Sewage Sludge. *EPA/625/R-92/013*. Revised July 2003, p. 7, 13, 26, 32, 54, 58, 61.

U.S.EPA. Water Efficiency Technology Fact Sheet Composting Toilets. *EPA 832-F-99-066*. September 1999, p. 6.

DEANGELIS/KRISTEN M., et al. Characterization of Trapped Lignin-Degrading Microbes in Tropical Forest Soil. http://doi.org/10.1371/journal.pone.0019306. 2011, p. 1.

HOLWERDA/E K, Ellis L D, Lynd L R, et al. Development and Evaluation of methods to Infer Biosynthesis and Substrate Consumption in Cultures of Cellulolytic Microorganisms. *Biotechnology and Bioengineering*. 2013, p. 4.

What is claimed is:

1. A thermophilic enzymatic biosynthesis device for a dry closet, which produces outputs of newly synthesized substances, stabilized matter and fully recovered organic material, whereby organic solid, liquid and gaseous waste are treated, comprises:
   a) a multiphase thermophilic environment chamber which accommodates several zones and a thermodynamic pathway located above and coupled to said multiphase thermophilic environment chamber;
   b) a subterranean uptake chamber which is adjacent to the multiphase thermophilic environment chamber; and
   c) an ammine reaction chamber which is positioned to have association with the multiphase thermophilic environment chamber and said subterranean uptake chamber.

2. The thermophilic enzymatic biosynthesis device according to claim 1, wherein the multiphase thermophilic environment chamber comprises:
   a) a mixing zone comprising a base and a containment wall;
   b) a germination zone comprising a counter blade coupled to a stockpile wall segment and a collection-distribution area having communication with said mixing zone;
   c) a cultivation zone comprising a separation wall coupled to an accumulation wall, wherein said separation wall includes an open base and said accumulation wall is fixed to a bottom plate, wherein said cultivation zone, further comprises a collection area partially defined by said open base, which has communication with the mixing zone; and
   d) a mixing blade connected to a vertical rotational shaft centered in the mixing zone, wherein, said mixing blade initiates activity within the mixing zone, said collection-distribution area and said collection area.

3. The thermophilic enzymatic biosynthesis device according to claim 2, wherein:
   a) said germination zone comprises said counter blade and said stockpile wall segment; and
   b) wherein the counter blade and the stockpile wall together define a sporulation area adjacent to the collection-distribution area.

4. The thermophilic enzymatic biosynthesis device according to claim 2, wherein the mixing blade comprises:
   a) a flat edge and a shaped edge;
   b) wherein the mixing blade has upward interaction within the collection-distribution area and the collection area when said flat edge leads in rotational motion; and
   c) wherein the mixing blade has downward interaction within the collection-distribution area when said shaped edge leads in rotational motion.

5. The thermophilic enzymatic biosynthesis device according to claim 2, wherein the cultivation zone comprises;
   a) a mixing device and an accumulation area extending above the separation wall; and
   b) wherein said accumulation area accommodates treated solids.

6. The thermophilic enzymatic biosynthesis device according to claim 1, wherein the multiphase thermophilic environment chamber which further comprises:
   a) a pasteurization zone comprises an isolation base which is connected to an isolation wall, which has a recovery passageway, wherein said pasteurization zone further comprises a platform and a transport blade;
   b) wherein said transport blade is fixed to said vertical rotational shaft and has rotational interaction with the accumulation area, said platform and said pasteurization zone;
   c) wherein the platform is joined to said isolation wall associated with the pasteurization zone and is joined to the separation wall associated with the cultivation zone; and
   d) wherein the mixing blade passes beneath said isolation base separately from the pasteurization zone.

7. The thermophilic enzymatic biosynthesis device according to claim 1, wherein said thermodynamic pathway comprises:
   a) a sloping surface where two adjacent sides of said sloping surface define an ascending trough;
   b) wherein said ascending trough has interaction with a hearth frame; and
   c) wherein said hearth frame includes a condensation receptacle and a flue passageway.

8. The thermophilic enzymatic biosynthesis device according to claim 1, further comprises a deposit zone that includes:
   a) a chute, a disposal tray and a urine diversion channel;
   b) wherein said disposal tray has a collection surface and a pivotal edge;
   c) wherein said urine diversion channel has positional association with said pivotal edge; and
   d) wherein said chute is configured to accommodate the urine diversion channel and the disposal tray.

9. The thermophilic enzymatic biosynthesis device according to claim 1, wherein the subterranean uptake chamber comprises:
   a) an uptake passageway connected to a dispersion cartridge;

b) a bottom surface connected to at least one a retention wall; and c) a plant growth medium and a plant having an uptake root structure; and d) wherein said dispersion cartridge diffuse gases into said plant growth medium and said uptake root structure.

10. The thermophilic enzymatic biosynthesis device according to claim 1, wherein said ammine reaction chamber comprises:

a) an oxidation surface within a casing;

b) a first orifice coupling;

c) a second orifice coupling; and d) a metal ammine complex drain;

e) wherein said first orifice coupling is coupled to said flue passageway associated with the thermodynamic pathway; and f) wherein said second orifice coupling is joined to said uptake passageway associated with the subterranean uptake chamber.

11. The thermophilic enzymatic biosynthesis device according to claim 10, wherein:

a) the ammine reaction chamber allows gaseous vapor to pass through;

b) said oxidation surface has contact with condensing vapors; and c) wherein the oxidation surface has reactivity with ammonia and ammonium.

12. The thermophilic enzymatic biosynthesis device according to claim 1, further comprises a housing structure that includes:

a) a lower housing subassembly and an upper housing subassembly;

b) wherein said lower housing subassembly accommodates the multiphase thermophilic environment chamber; and c) wherein said upper housing subassembly accommodates the thermodynamic pathway, the subterranean uptake chamber and the ammine reaction chamber.

13. The thermophilic enzymatic biosynthesis device according to claim 1, wherein the multiphase thermophilic environment chamber comprises:

a) a multiphase germination which is accommodated by but not limited to said sporulation area, the mixing zone and the cultivation zone;

b) a functional respiration, which is accommodated by the thermodynamic pathway; and c) wherein said multiphase germination and said functional respiration together have convective interaction with the multiphase thermophilic environment chamber, the ammine reaction chamber and the subterranean uptake chamber.

* * * * *